United States Patent
Purich

(10) Patent No.: US 11,406,718 B2
(45) Date of Patent: Aug. 9, 2022

(54) METHODS OF DETECTING PANCREOBILIARY DUCTAL LEAKS

(71) Applicant: Edward E. Purich, Laurel, MD (US)

(72) Inventor: Edward E. Purich, Laurel, MD (US)

(73) Assignee: CHIRHOCLIN, INC., Burtonsville, MD (US)

( * ) Notice: Subject to any disclaimer, the term of this patent is extended or adjusted under 35 U.S.C. 154(b) by 0 days.

(21) Appl. No.: 13/893,676

(22) Filed: May 14, 2013

(65) Prior Publication Data

US 2013/0323174 A1 Dec. 5, 2013

Related U.S. Application Data

(60) Provisional application No. 61/652,356, filed on May 29, 2012.

(51) Int. Cl.
*A61K 49/00* (2006.01)

(52) U.S. Cl.
CPC .................. *A61K 49/0004* (2013.01)

(58) Field of Classification Search
None
See application file for complete search history.

(56) References Cited

U.S. PATENT DOCUMENTS

| | | | |
|---|---|---|---|
| 4,246,374 A | 1/1981 | Kopchik | |
| 4,278,751 A | 7/1981 | Specht et al. | |
| 4,366,228 A | 12/1982 | Specht et al. | |
| 4,491,628 A | 1/1985 | Ito et al. | |
| 4,548,891 A | 10/1985 | Riediker et al. | |
| 4,585,876 A | 4/1986 | Fischer et al. | |
| 4,681,959 A | 7/1987 | Ayen et al. | |
| 5,019,482 A | 5/1991 | Ai et al. | |
| 5,049,628 A | 9/1991 | Nawata et al. | |
| 5,215,863 A | 6/1993 | Nawata et al. | |
| 5,492,793 A | 2/1996 | Breyta et al. | |
| 5,538,821 A | 7/1996 | Kakinuma et al. | |
| 5,545,702 A | 8/1996 | Oishi et al. | |
| 6,042,997 A | 3/2000 | Barclay et al. | |
| 6,284,185 B1 | 9/2001 | Tokuda et al. | |
| 6,294,239 B1 | 9/2001 | Tokuda et al. | |
| 6,524,708 B2 | 2/2003 | Puligadda et al. | |
| 6,602,646 B1 | 8/2003 | Sato et al. | |
| 6,730,452 B2 | 5/2004 | Brock et al. | |
| 7,282,324 B2 | 10/2007 | Weber et al. | |
| 7,358,027 B2 | 4/2008 | Ito et al. | |
| 7,359,108 B2 | 4/2008 | Hayes et al. | |
| 7,381,698 B2 | 6/2008 | Fein et al. | |
| 7,459,155 B2 | 12/2008 | Margolin et al. | |
| 7,479,364 B2 | 1/2009 | Ito | |
| 7,800,816 B2 | 9/2010 | Hayes et al. | |
| 7,813,030 B2 | 9/2010 | Lo et al. | |
| 7,947,285 B2 | 5/2011 | Fein et al. | |
| 2005/0002922 A1* | 1/2005 | Boismenu | A61K 38/2235 424/94.2 |
| 2005/0070472 A1 | 3/2005 | Gedulin et al. | |
| 2005/0129675 A1 | 6/2005 | Fein et al. | |
| 2006/0002912 A1 | 1/2006 | Fein et al. | |
| 2006/0019347 A1 | 1/2006 | Cho et al. | |
| 2007/0219222 A1 | 9/2007 | Moran et al. | |
| 2008/0146611 A1 | 6/2008 | Moran et al. | |
| 2009/0081184 A1 | 3/2009 | Margolin et al. | |
| 2009/0143377 A1 | 6/2009 | Ng et al. | |
| 2009/0192558 A1 | 7/2009 | Whitehurst et al. | |
| 2010/0048472 A1 | 2/2010 | Rosen et al. | |
| 2010/0197586 A1 | 8/2010 | Bevec et al. | |
| 2010/0204313 A1 | 8/2010 | Pasricha | |
| 2014/0349939 A1 | 11/2014 | Purich | |

OTHER PUBLICATIONS

Akisik et al., Dynamic Secretin enhanced MR Cholangiopancreatography, RadioGraphics 2006; 26:665-677.*
Demirjian et al., The inconsistent nature of symptomatic pancreatico-jejunostomy anastomotic structures, HPB Dec. 2010, 482-487.*
Callery et al., Prevention and Management of Pancreatic Fistula, J Gastrointest Surg (2009) 13:163-173.*
Spanos et al., Bile leaks from the duct of Luschka (subvesical duct): a review, Arch Surg (2006) 391: 441.*
Barnum et al., The use of pancreatic ductoscopy in the operative management of benign and malignant pancreatic disorders, Surg Endosc (1995) 9: 53-55.*
Gillams et al., Diagnosis of Duct Disruption and Assessment of Pancreatic Leak with Dynamic Secretin-Stimulated MR Cholangiopancreatography, AJR 2006; 186:499-506.*
Yamaguchi et al., Litmus Paper Helps Detect Potential Pancreatoenterostomy Leakage, Am J Surg. 1998;175:227-228. (Year: 1998).*
Matos, MD, Celso et al., "Pancreatic Duct: Morphologic and Functional Evaluation with Dynamic MR Pancreatography after Secretin Stimulation", Radiology, vol. 203, pp. 435-441 (May 1997).
Fukukura, MD, Yoshihiko et al., "Pancreatic Duct: Morphologic Evaluation with MR Cholangiopancreatography after Secretin Stimulation", Radiology, vol. 222, No. 3, pp. 674-680 (Mar. 2002).
Monill, Josep et al., "Pancreatic Duct After Pancreatoduodenectomy: Morphologic and Functional Evaluation with Secretin-Stimulated MR Pancreatography", AJR, vol. 183, pp. 1267-1274 (Nov. 2004).
Gillams, A. R. et al., "Diagnosis of Duct Disruption and Assessment of Pancreatic Leak with Dynamic Secretin-Stimulated MR Cholangiopancreatography", AJR, vol. 186, pp. 499-506 (Feb. 2006).

(Continued)

*Primary Examiner* — Jennifer Lamberski

(74) *Attorney, Agent, or Firm* — Cantor Colburn LLP

(57) ABSTRACT

The present invention is directed to a method for identifying ductal leaks during pancreobiliary surgery in a human patient. The invention comprises the steps of: administering to a human patient undergoing pancreobiliary surgery an effective amount of a pharmaceutical composition comprising secretin and a pharmaceutically acceptable carrier; and observing the patient during the surgery for the presence of pancreobiliary ductal leaks.

13 Claims, No Drawings

(56) References Cited

OTHER PUBLICATIONS

Imamura, MD, Masayuki et al., "Use of Selective Arterial Secretin Injection Test to Guide Surgery in Patients with Zollinger-Ellison Syndrome", World Journal of Surgery, vol. 17, No. 4, pp. 433-438 (Jul./Aug. 1993).
Gibril, MD, Fathia et al., "Metastatic Gastrinomasa: Localization with Selective Arterial Injection of Secretin", Radiology, vol. 198, No. 1, pp. 77-84 (Jan. 1996).
Heverhagen, PhD, Md, Johannes et al., "Pancreatic Transplants: Noninvasive Evaluation with Secretin-augmented MR Pancreatography and MR Perfusion Measurements—Preliminary Results", Radiology, vol. 233, No. 1, pp. 273-280 (Oct. 2004).
Fattahi, MD, Rana et al., "Magnetic Resonance Imaging in Pancreas Transplantation", Top MAGN RESON Imaging, vol. 20, No. 1, pp. 49-55 (Feb. 2009).
Boraschi, Piero et al., "Pancreatic transplants: secretin-stimulated MR pancreatography", Abdominal Imaging, vol. 32, pp. 207-214 (Mar. 2007).
Abstract of Russian Federation SU 624635, 1978.
Acute and Chronic Pancreatitis (enclosed pp. 1-16 available online Oct. 30, 2009, from http://web.archive.org/web/20091030012855/ http://rezidentiat.3x.ro/eng/pancreatitaeng.htm).
Chey et al.; "Secretin Historical Perspective and Current Status"; Pancreas, vol. 43, No. 2; Mar. 2014; pp. 162-182.
Guy et al.; "Protein Content of Precipitates Present in Pancreatic Juice of Alcoholic Subjects and Patients with Chronic Calcifying Pancreatitis"; Gastroenterology; vol. 84; Jan. 1983; pp. 102-107.
International Preliminary Report on Patentability and Written Opinion of the International Searching Authority for International Patent Application No. PCT/US2013/025820; dated Aug. 19, 2014; 6 Pages.
International Search Report for International Patent Application No. PCT/US2013/025820 International Filing Date: Feb. 13, 2013; dated Apr. 23, 2013; 2 Pages.
Kiem et al.; "Failure of Secretin to Prevent or Ameliorate Cerulein-induced Pancreatitis in the Rat"; Hepatogastroenteroiogy; vol. 32; 1985; pp. 91-96.

Kuiper et al.; "Diagnostic Efficacy of the Secretin Stimulation Test for the Zollinger-Ellison Syndrome: An Intra-Individual Comparison Using Different Dosages in Patients and Controls"; Pancreatology; vol. 10; 2010; pp. 14-18.
Lankisch et al.; "Influence of Secretin on the Course of Acute Experimental Pancreatis in Rats"; Digestion; vol. 26; 1983; pp. 187-191.
M. R. Goulden, The pain of chronic pancreatities: a persisten clinical challenge, The British Pain Society; British Journal of Pain, vol. 1, No. 1, 2013, pp. 8-22.
Madsen et al.; "The intraductal Pancreatic Pressure in Chronic Obstructive Pancreatitis"; Scand. J. Gastroenterol.; vol. 17; 1982; pp. 553-554.
Mass of an Adult, from https://hypertextbook.com/facts/2003/ AlexSchlessingerman.shtml, pp. 1-4, accessed Aug. 6, 2017.
Noda et al.; "Bromhexine Hydrochloride Eliminates Protein Plugs and Relieves Attacks of Pancreatitis"; Pancreas; col. 15, No. 2; 1997; pp. 209-2011.
Renner et al.; "Protective Effects of Exogenous Secretin on Ceruletide-induced Acute Pancreatitis in the Rat"; J. Clin. Invest.; vol. 72; Sep. 1983; pp. 1081-1092.
Shinohara et al.; "A case of mucin-producing bile duct tumor which responded to bromhexine hydrochloride treatment and radiotherapy"; Tando; vol. 7; 1993; pp. 527-534.
Tsujimoto et al.; "Effect, of Bromhexine Hydrochloride Therapy for Alcholic Chronic Pancreatitis"; Alcohol. Clin. Exp. Res.; vol. 29, No. 12; Dec. 2005; pp. 272S-276S.
Tympner et al., "The Treatment of Chronic Recurrent Pancreatitis with Depot Secretin—a Preliminary Report" Hepato-gastroenterol, 33, (1986), pp. 159-162.
Tympner et al.; "Viscosity and Trypsin Activity of Pure Pancreatic Juice in Chronic Pancreatitis"; Acta Hepatogastroenterol.; vol. 25; 1978; pp. 73-76.
Yamamoto et al.; "Double Doses of Secretin Contribute to Diagnosis of Zollinger-Ellison Syndrome in Secretin adn Selective Arterial Secretion Injection Tests—A Case Report"; Digestive Dis. and Sci.; vol. 50 No. 11; Nov. 2005; pp. 2034-2036.

* cited by examiner

METHODS OF DETECTING PANCREOBILIARY DUCTAL LEAKS

BACKGROUND OF THE INVENTION

1. Field of the Invention

The invention relates generally to methods for detecting pancreobiliary ductal leaks, and more specifically to methods for detecting pancreobiliary ductal leaks during or shortly after various pancreobiliary surgeries and prior to closing the surgical wounds on the abdominal cavity of the patient. The methods comprise administering an effective amount of a pharmaceutical composition comprising human or porcine secretin and a pharmaceutically acceptable carrier.

2. Brief Description of the Related Art

Pancreobiliary surgery can treat a wide variety of conditions including pancreatic cancer, cysts of the pancreas, chronic pancreatitis, and acute pancreatitis, and encompasses a wide variety of surgical procedures. The majority of surgical procedures performed on the pancreas involve resection (removal) of the portion that is involved in the disease process. These types of surgeries include the Whipple Procedure (the most common surgical treatment for cancers involving the head of the pancreas), distal pancreatectomy (resection of tumors of the tail of the pancreas), and total pancreatectomy (removal of the entire pancreas and the spleen), to name a few. Other pancreobiliary surgeries, such as pancreatic transplantation or surgery on the pancreas due to injury, are also becoming more common.

In many cases, these surgeries involve suturing various tissues together, including pancreobiliary ductal tubing. Since the pancreas is responsible for producing important hormones, as well as secreting pancreatic juice containing digestive enzymes, any leaks that are present in these sutures can present serious complications in the surgery. The ability to observe or detect these leaks at an early stage has become an important consideration in the overall success of the surgery.

Current methods of visualizing the features of the pancreobiliary duct and related structures utilize various types of imaging techniques. In some cases, administration of secretin was also employed to stimulate the secretion of fluid and bicarbonate by the exocrine pancreas to increase the volume of fluid in the pancreobiliary duct, and thereby improve the sonographic depiction. For example, magnetic resonance (MR) cholangiopancreatography is a non-invasive imaging technique that accurately depicts the morphologic features of the biliary and pancreobiliary ducts. In several studies (Matos, C. et al., Radiology 203:435-441, 1997; Fukukura, Y. et al., Radiology 222:674-680, 2002), dynamic magnetic resonance cholangiopancreatography was used in combination with administration of secretin to show the delineation of ductal morphologic features in the patients. The combination of secretin and MR cholangiopancreatography has also been used as a diagnostic tool in surgical evaluations (Montill, J. et al., AJR 183:1267-1274, 2004) diagnosis of duct disruption (Gillams, A. et al., AJR 186:499-506, 2006) and cancer diagnosis and localization (Imamura, M. et al., World J. Surg. 17:433-438, 1993; Gibril, F. et al., Radiology 198:77-84, 1996). The combination of secretin and MR pancreatography has also been used in evaluations of pancreas transplant procedures (Heverhagen, J. et al., Radiology 233:273-280, 2004; Fattahi, R. et al., Top. Magn. Reson. Imaging 20(1):49-55, 2009; Boraschi, P. et al., Abdom Imaging 32:207-214, 2007).

A major disadvantage of the prior diagnostic procedures is that in order to perform the necessary imaging, the patient must have completed the surgery and the wound closed. However, if there is a later determination of ductal leakage, for example by the above cited procedures, it would require another round of surgery to open the abdominal cavity of the patient and address the leakage. It would be advantageous to identify ductal leaks in real time during surgery, and prior to closing of the abdominal cavity, in order to minimize additional surgeries, provide faster recovery, and prevent additional trauma to the patient. The present invention is believed to be an answer to that need.

SUMMARY OF THE INVENTION

In one aspect, the present invention is directed to a method for identifying ductal leaks during pancreobiliary surgery in a human patient, comprising the steps of: administering to a human patient undergoing pancreobiliary surgery an effective amount of a pharmaceutical composition comprising secretin and a pharmaceutically acceptable carrier; and observing the patient during the surgery for the presence of pancreobiliary ductal leaks.

This and other aspects will become apparent upon reading the following detailed description of the invention.

DETAILED DESCRIPTION OF THE INVENTION

It has now been unexpectedly found that secretin is effective for identifying ductal leaks during pancreobiliary surgery in a human patient.

In accordance with one embodiment of the method of the present invention, ductal leaks may be identified in a patient undergoing pancreobiliary surgery by administering to that patient a pharmaceutical composition comprising secretin. Patients subjected to the method of the present invention can benefit from the administration of intravenous secretin to help identify ductal leaks during surgery where they are most efficiently addressed. As described in more detail below, secretin acts to increase the volume and bicarbonate content of pancreobiliary juice and to increase the pancreobiliary duct diameter. These effects make identification of ductal leaks during surgery much more efficient and immediate than prior methods that rely on post-operative imaging technologies and subsequent surgeries. Once identified, the surgeon can immediately fill or cauterize the ductal leaks during the pancreobiliary surgical process. Thus, the present invention offers the advantages of identifying ductal leaks in real time during surgery, and prior to closing of the abdominal cavity of the patient, in order to minimize additional surgeries, provide faster recovery, and prevent additional trauma to the patient.

As indicated above, the present invention is directed to a method for identifying ductal leaks during pancreobiliary surgery by administering an effective amount of a pharmaceutical composition comprising secretin and a pharmaceutically acceptable carrier to a patient undergoing pancreobiliary surgery in order to identify ductal leakage during surgery. Each of these components is discussed in more detail below.

Secretin is a 3055.5 MW (27 amino acid) gastrointestinal peptide hormone originally extracted from the porcine duodenum. The primary action of secretin is to increase the volume and bicarbonate content of pancreatic juice (Gutierrez L V, et al., Gut 13:721-25 (1972); Laugier R, et al., Digestion 54:54-60 (1993); Cavallini G, et al., Dig. Dis. Sci. 37(1):93-96 (1992)). also increases the pancreatic duct diameter (Glaser J, et al., Int. J. Pancreatol. 15:195-200 (1994); Tulassay Z, et al., Gastroenterol. J. 51:47-50 (1991)) and causes sphincter of Oddi relaxation (Geenen J E et al., Gastroenterology 78:317-24 (1980); Laugier R. Endoscopy 26:222-27 (1994)). In the methods of the invention, secretin may be used from any source. Preferably the secretin used in the methods of the present invention is the naturally occurring form, the synthetic form, or the genetically recombined form of porcine, bovine or human secretin. Biologically derived secretin (e.g., extracted from tissue) may also be used. A porcine form of secretin is sold under the tradename "SECRELUX". One useful form of naturally occurring human secretin is manufactured by ChiRhoClin, Inc. (Burtonsville, Md.) with the tradename "CHIRHOSTIM". One useful form of porcine secretin is manufactured by ChiRhoClin, Inc. (Burtonsville, Md.) and sold under the trade name "SECREFLO" by Repligen Corporation (Waltham, Mass.). Another useful form of porcine secretin is manufactured by ChiRhoClin, Inc. (Burtonsville, Md.) with the tradename "SECREMAX". A useful form of human secretin is manufactured and sold by ChiRhoClin, Inc. under the tradename "SECRETIN-HUMAN".

Secretin has been safely demonstrated at a dose of 6 U/kg (1.2 mcg/kg) for intravenous administration (Yamamoto, Digestive Dis. And Sci. 50:2034-2036 (November 2005)). 0.78 mcg/kg was safely given to 12 patients suffering from Zollinger-Ellison Syndrome (ZES), and these findings were confirmed in a validation cohort study (Kuiper, Pancreatology 10(1):14-18 (2010); EPub 19 Mar 2010). The largest parental dose of secretin administered in a study was 160 mcg twice a day per patient for 7 days. This dosing regimen was found safe and is at least 333% more than the highest dosing in this study. The 333% dose was administered for 7 consecutive days without consequences.

The secretin may be combined with a pharmaceutically acceptable carrier to form a pharmaceutical composition. Thus, the pharmaceutical compositions of this invention comprise secretin from any source (including pharmaceutically acceptable salts thereof) in combination with any pharmaceutically acceptable carrier, adjuvant or vehicle. Pharmaceutically acceptable carriers, adjuvants and vehicles that may be used in the pharmaceutical compositions of the present invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered by any route that produces acceptable bioavailability. Suitable administration methods include, but are not limited to, parenteral methods such as intravenous, intra-arterial, subcutaneous and intramuscular and per os (by mouth), or sublingual, and transdermal bolus or continuous infusions of secretin may be used. Particularly useful methods of administration in accordance with the method of the invention include oral, intravenous, and intra-arterial methods. The risks associated with the use of intravenous secretin administration are minor. There has not been any serious reported adverse drug reaction to human secretin stimulation. Rarely, in the thousands of patients who have undergone pancreobiliary function testing with human secretin, there is flushing of the face with stable vital signs. Therefore, the risk of administrating secretin is minimal. Secretin is also not known to increase the risk of acute pancreatitis episodes in patients with CP and acute recurrent pancreatitis (ARP) not presently having an acute pancreatitis attack. No allergic reactions have been reported with secretin in commercial use although the administration of a test dose 0.2 mcg (0.1 mL) IV is still recommended. No significant hemodynamic effects have been observed following administration of secretin. Otherwise the risks of administering secretin are minimal.

The pharmaceutical compositions of the invention are preferably administered internally, e.g., intravenously, in the form of conventional pharmaceutical preparations, for example in conventional enteral or parenteral pharmaceutically acceptable excipients containing organic and/or inorganic inert carriers, such as water, gelatin, lactose, starch, magnesium stearate, talc, plant oils, gums, alcohol, VASELINE (petroleum jelly), or the like. The pharmaceutical preparations can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

The pharmaceutical preparation of the invention should include an amount of secretin effective for visually identifying ductal leakage during surgery. The effective dosage will depend on several factors, including body weight, body mass index, formulation factor, route of administration, age, gender, disease severity, and the like. Suitable dosages may be, for example, in the range of about 2 to 80 micrograms secretin, more preferably of about 8 to about 36 micrograms secretin, and most preferably between 15 and 20 micrograms secretin per dose administered via intravenous bolus. In terms of body weight, suitable dosages of the pharmaceutical composition preferably range from about 0.1 µg secretin per kg body weight to about 0.4 µg secretin per kg body weight, and more preferably 0.15 µg secretin per kg body weight to about 0.3 µg secretin per kg body weight. One particularly effective dose is 0.2 µg per kg body weight. As will be appreciated by those skilled in the art, multiple doses of secretin may be required to be administered each day over a period of time (for example, a dose of 16 micrograms secretin (approximately 0.2 micrograms per kilogram body weight) intravenously, four times per day for 7 days.

In order to achieve the above dosage ranges, it will be appreciated by those of skill in the art that the amount of secretin used with a particular form of administration will depend on absolute bioavailability of the secretin dosage and the route of administration. For example, a transdermal patch requires approximately 1 mg of secretin to achieve dosages in the above ranges. A nasal spray requires approximately 2 mg secretin per spray in order to achieve the above dosage ranges. A sublingual tablet or film requires approximately 50 mg secretin to achieve the above dosage ranges, and a tablet or capsule requires approximately 100-250 mg secretin per tablet or capsule to achieve the above dosage ranges.

The method of the invention may be used in any surgery where ductal leakage can occur, and particularly during various types of surgery involving the pancreas, such as pancreatic transplant, duodectomy, removing or rerouting pancreatic ductal tubes, and the like. Examples of surgeries where the method of the invention could be useful include, but are not limited to, the Whipple Procedure, distal pancreatectomy, total pancreatectomy, pancreatic transplantation or surgery on the pancreas due to injury (e.g., gun shot, car accident, and the like). It will be appreciated that the invention may also be implemented broadly in any type of pancreobiliary surgery, such as any procedure that relates to the common bile duct and/or gall bladder.

Following identification of the pancreobiliary ductal leakage, the leakage can be repaired using conventional techniques, including but not limited to filling, cauterization, suturing, gluing, sewing, clipping, and the like.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A method for identifying ductal leaks during pancreobiliary surgery in a human patient, comprising the steps of:
   administering to a human patient undergoing pancreobiliary surgery an effective amount of a pharmaceutical composition to visually identify ductal leakage during said pancreobiliary surgery, said pharmaceutical composition comprising secretin and a pharmaceutically acceptable carrier; wherein the effective amount of secretin administered to said patient in said pharmaceutical composition ranges from 0.1 to 0.4 micrograms per kilogram bodyweight of said patient;
   observing said patient during said pancreobiliary surgery for the presence of ductal leaks;
   identifying said ductal leaks during said pancreobiliary surgery in said human patient; and
   repairing said ductal leaks identified during said pancreobiliary surgery and prior to completion of said surgery;
   wherein said method is implemented without the use of imaging techniques.

2. The method of claim 1, wherein said pancreobiliary surgery is selected from the group consisting of the Whipple Procedure, distal pancreatectomy, total pancreatectomy, pancreatic transplantation, surgery on the pancreas due to injury, duodectomy, removing or rerouting pancreatic ductal tubes, and combinations thereof.

3. The method of claim 1, wherein the effective amount of secretin administered to said patient in said pharmaceutical composition ranges from 0.15 to 0.3 micrograms per kilogram bodyweight of said patient.

4. The method of claim 1, wherein the effective amount of secretin administered to said patient in said pharmaceutical composition is approximately 0.2 micrograms per kilogram bodyweight of said patient.

5. The method of claim 1, wherein said secretin is a naturally occurring form of secretin.

6. The method of claim 1, wherein said secretin is a synthetic form of secretin.

7. The method of claim 6, wherein said synthetic form of secretin is synthetic porcine secretin.

8. The method of claim 1, wherein said secretin is a genetically recombined form of porcine, bovine, or human secretin.

9. The method of claim 1, wherein said secretin is synthetic human secretin (sHS).

10. The method of claim 1, wherein said administration step comprises intravenous administration.

11. The method of claim 1, wherein said administration step comprises oral administration.

12. The method of claim 1, wherein said pharmaceutically acceptable carrier is selected from the group consisting of ion exchangers, alumina, aluminum stearate, lecithin, serum proteins, human serum albumin, phosphates, glycine, sorbic acid, potassium sorbate, partial glyceride mixtures of saturated vegetable fatty acids, water, salts, electrolytes, protamine sulfate, disodium hydrogen phosphate, potassium hydrogen phosphate, sodium chloride, saline, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

13. The method of claim 1, wherein said repairing step comprises a method selected from filling, cauterization, suturing, gluing, sewing, clipping, or a combination thereof.

* * * * *